United States Patent [19]
Koufman

[11] Patent Number: 5,879,897
[45] Date of Patent: Mar. 9, 1999

[54] METHODS AND COMPOSITIONS FOR THE DIAGNOSIS OF EXTRAESOPHAGEAL GASTRIC REFLUX

[75] Inventor: James Koufman, Winston-Salem, N.C.

[73] Assignee: Wake Forest University, Winston-Salem, N.C.

[21] Appl. No.: 717,793

[22] Filed: Sep. 23, 1996

[51] Int. Cl.[6] .......................... C12Q 1/37; G01N 33/573
[52] U.S. Cl. .............................. 435/7.4; 435/7.9; 435/23; 436/518
[58] Field of Search ................................ 435/7.4, 7.9, 23; 436/518

[56] References Cited

U.S. PATENT DOCUMENTS

| | | | |
|---|---|---|---|
| 4,668,621 | 5/1987 | Doellgast | 435/13 |
| 4,923,819 | 5/1990 | Fernandez et al. | 436/518 |
| 5,236,849 | 8/1993 | Ishikawa | 436/540 |
| 5,354,657 | 10/1994 | Höltke et al. | 435/6 |

OTHER PUBLICATIONS

D. C. Gotley et al, Gut, 32, 1093–1099, 1991.

International Search Report dated Feb. 20, 1998.

Axelsson, C. K., M. D. Nielsen, and A. M. Kappelgaard. "Solid–phase double–antibody radioimmunoassay of pepsinogen I in serum," *Clin. Chim. Acta.*, 121: 309–319, 1982.

Baccino, E., Le Goff, D., Lancien, G., et al.: "Exploration of Acid Gastroesophageal Reflux by 24–h pH Metry in Infants at Risk of Sudden Infant Death Syndrome: A Study of 50 Cases," *Forensic Sci Int*, 36: 225–260, 1988.

Doellgast, G. J. Triscott M. X., Beard G. A., Bottoms J. D., Roh B. H., Roman M. G., Hall P. A., Brown J. E. "Sensitive ELISA for detection of C. botulinum neurotoxins A, B and E using signal amplification via enzyme–linked coagulation assay," *J Clinical Microbiol* 31: 2402–2409, 1993.

Doellgast, G. J., Beard G. A., bottoms J. D., Cheng T., Roh B. H., Roman M. G., Hall P. A., Triscott M. X. "Enzyme–linked immunoabsorbent assay and enzyme–linked coagulation assay for detection of C. botulinum neurotoxins A, B and E and solution–phase complexes with dual–label antibodies," *J Clinical Microbiology* 32: 105–111, 1994.

Flores TC, Cross FS, Jones RD. "Abnormal Esophageal Manometry in Globus Hystericus," *Ann Otol Rhinol Laryngol*, 90:383–386, 1981.

Herbst, J.J., Minton, S.D. and Book, L.S.: "Gastroesophageal Reflux Causing Respiratory Distress and Apnea in Newborn Infants," *J Pediatr,* 95:763–768, 1979.

Huang, S. C., K. Miki, C. Furihata, M. Ichinose, A. Shimizu and H. Oka. "Enzyme–linked immunosorbent assays for serum pepsinogens I and II using monoclonal antibodies— with data on peptic ulcer and gastric cancer," *Clin Chim Acta* 175: 37–50, 1988.

Huang, S. C., K. Miki, K Hirano et al. "Enzyme–linked immunosorbent assay of serum pepsinogen I," *Clin Chim Acta* 162: 85–96, 1987.

Kalinovsky et al. "Clinico–Radiological and Fibergastroscopic correlations in the Diagnosis of Different Forms of Gastric Cancer Growth," *VOPR. ONKOL* (USSR), 24:7:41–46, 1978.

Konturek et al. "Effect of somatostatin on meal induced gastric secretion in duodenal ulcer patients," *Am J Dig Dis* 22(11)981–988, 1977.

Koufman JA, Wiener GJ, Wu WC, Castell DO. "Reflux laryngitis and its sequelae: the diagnostic role of ambulatory 24–hour pH monitoring," *J Voice* 2:78–89, 1988.

Koufman JA. "Editorial: Aerodigestive Manifestations of Gastroesophageal Reflux: What We Don't Yet Know," *Chest* 104:1321–1322, 1993.

Koufman JA. "The otolaryngologic manifestations of gastroesophageal reflux disease," *Laryngoscope* 101: (Supplement 53) 1–78, 1991.

Morrison MD. "Is chronic gastroesophageal reflux a causative factor in glottic carcinoma?" *Otolaryngol Head Neck Surg* 99:370–373, 1988.

Ohman L, Olofsson J, Tibbling L, et al. "Esophageal Dysfunction in Patients with Contact Ulcer of the Larynx," *Ann Otol Rhinol Laryngol* 92:228–230, 1983.

Olson NR. "The Problem of Gastroesophageal Reflux," *Otolaryngol Clin North Am* 19:119–133, 1986.

Ossakow SJ, Elta G, Colturi T, et al.: "Esophageal reflux and dysmotility as the basis for persistent cervical symptoms," *Ann Otol Rhinol Laryngol* 96:387–392, 1987.

Paton, J.Y., MacFadyen, U.M. and Simpson, H.: "Sleep Phase and Gastro–oesophageal Reflux in Infants at Possible Risk of SIDS," *Arch Dis Child,* 64:264–269, 1989.

Richter JE, Bradley LA, DeMeester TR, Wu WC, et al.: "Normal 24–Hour pH values: Influence of study center, pH electrode, age, and gender," *Dig Dis Sci* 37:849–856, 1992.

Richter JE, ed. "Ambulatory Esophageal pH Monitoring: Practical Approach and Clinical Applications," Igaku–Shoin, Tokyo, 1991. Table of Contents Only.

Sekera et al. "Sécrétion gastique de pepsine dans le reflux gastro–oesophagien compliqué ou non d'oesophagite peptique," *Gastroenterol Clin Biol.* (France) 16(2) 141–7, 1992.

Taggart and Samloff *Gastroenterology* Jan. 1987, 92(1) 143–150.

Waldum HL, Straume BK, Burhol PG. "Radioimmunoassay of group I pepsinogens (PG I) and the effect of food on serum PG I," *Scand J Gastroenterl* 14: 241–247, 1979.

Ward PH, Hanson DG. "Reflux as etiological factor of carcinoma of the laryngopharynx," *Laryngoscope* 98:1195–1199, 1988.

Wiener GJ, Cooper JB, Wu WC, et al. "Is hoarseness an atypical manifestation of gastroesophageal reflux (GER)! An ambulatory 24 hour pH study," (Abstract) *Gastroenterol* 90A:1691, 1986.

(List continued on next page.)

*Primary Examiner*—David Saunders
*Attorney, Agent, or Firm*—Arnold, White & Durkee

[57] ABSTRACT

Disclosed are methods of detecting a gastric reflux in the esophagus or in the throat of a subject. The basis of the method is the detection of the presence of pepsin or pepsinogen at higher than normal levels. Detection is preferably by an immunoassay technique.

23 Claims, 2 Drawing Sheets

OTHER PUBLICATIONS

Wiener GJ, Koufman JA, Wu WC, Copper JB, Richter JE, Castell DO. "The pharyngo–esophageal dual ambulatory pH probe for evaluation of atypical manifestations of gastroesophageal reflux (GER)," *Gastroenterol* 92:A 1694, 1987.

Wiener GJ, Koufman JA, Wu WC, et al. "Chronic hoarseness secondary to gastroesophageal reflux disease: documentation with 24–hour ambulatory pH monitoring," *Am J Gastroenterol* 84:1503–1508, 1989.

International Search Report dated Jan. 26, 1998. (PCT/US97/17171).

METHODS AND COMPOSITIONS FOR THE DIAGNOSIS OF EXTRAESOPHAGEAL GASTRIC REFLUX

BACKGROUND OF THE INVENTION

1. Field of the Invention

The present invention relates generally to the fields of Otolaryngology, Gastroenterology, Anesthesiology, Pulmonology and critical care medicine, and more particularly, the fields of detection and diagnosis of esophageal and extraesophageal gastric reflux (EEGR).

2. Description of Related Art

Gastric reflux, and especially EEGR, influences the development, duration and/or outcome of most major airway (i.e. the laryngopharynx, tracheobronchial tree and lung) diseases (Koufman 1991). It has also been suggested that EEGR is a causal factor of asthma, chronic obstructive pulmonary disease, sudden infant death syndrome (SIDS) and laryngeal carcinogenesis (Baccino et al., 1988; Herbst et al., 1979; Paton et al., 1989; Morrison 1988; Ward and Hanson 1988; Koufman 1991).

Gastroesophageal reflux (GER) refers to the backflow of gastric contents into the esophagus. Some GER is normal; however, in individuals with excessive reflux, either in amount or in duration, GER causes significant suffering and tissue damage and is termed gastroesophageal reflux disease (GERD). GERD has a relatively broad spectrum of clinical manifestations but is essentially defined by the development of "peptic esophagitis" (esophageal inflammation, even ulceration, stricture, metaplasia, and neoplasia, as the result of excessive contact of the esophageal lining with gastric acid and pepsin, the principal digestive enzyme of the stomach).

It is estimated that 10% of all Americans have symptoms of heartburn and regurgitation daily and 30% have symptoms less frequently (Castell et al. 1987), but estimates of the number of Americans with reflux-related laryngeal, voice and airway disorders remains unknown, because people with EEGR often do not have esophagitis or heartburn (Koufman 1991). Thus, although it has been reported that two-thirds of patients with laryngeal and voice disorders have EEGR as either the primary causal agent or a significant etiological cofactor, the prevalence of these EEGR-related conditions remains unknown. It is estimated that EEGR may affect up to 50% of adult Americans over 40 years of age.

Yet the epidemiologies and natural histories of GERD remain incompletely understood because of a lack of sensitive and accurate diagnostic tools for detecting and distinguishing GERD from EEGR and other diseases of the esophagus, throat and airway. Gastroenterologists and otolaryngologists are currently forced to make diagnoses based on the principal clinical symptoms, e.g. heartburn for GERD and for hoarseness EEGR. However, less than half of all patients with EEGR into the laryngeal and pharyngeal regions (i.e. the throat), as documented by pH monitoring, complain of heartburn or regurgitation (Ossakow et al. 1987; Koufman et al 1988; Koufman 1991; Koufman 1993; Koufman 1996; Wiener et al. 1986; Wiener et al. 1987; Wiener et al. 1989). Thus, the principal difference in symptoms between EEGR and GERD patients appears to be that EEGR patients infrequently have heartburn, the primary symptom of esophagitis.

Patients with EEGR usually complain of throat symptoms such as hoarseness, a sensation of a lump in the throat,. chronic throat clearing, choking episodes, or throat pain, or sometimes pulmonary symptoms such as chronic cough and asthma (Ohman et al. 1983; Olson 1986; Wiener et al. 1986; Ossakow et al. 1987; Flores et al 1981). Esophagitis and heartburn usually occur in patients with supine nocturnal reflux but patients with EEGR generally experience upright daytime reflux (Koufman 1991; Wiener et al. 1989). In addition, patients with EEGR tend to have UES dysfunction, whereas typical esophagitis patients have predominantly lower esophageal sphincter (LES) dysfunction. Because the patterns and mechanisms of reflux in patients with EEGR appear to differ significantly from those of patients with GERD, patients with EEGR are frequently mis-diagnosed because they do not have esophagitis and its symptoms (Wiener et al. 1989; Koufnan 1991).

Several studies comparing symptoms, diagnostic data, and results of treatment of patients with EEGR with normal controls and with GERD (i.e. esophagitis) patients have been reported (Koufman 1991; Wiener et al. 1986; Ossakow, et al. 1987; Wiener, et al. 1989). Based upon the fact that similar diagnostic methods were used for all of these studies, a comparative profile of the two conditions, EEGR and GERD, is shown in Table 1. These composite profiles are derived from the GERD literature and the inventor's data.

TABLE 1

Summary of the Differences Between EEGR and GERD Patients

|  | EEGR | GERD |
| --- | --- | --- |
| Symptoms |  |  |
| Heartburn | 350% | 89% |
| Hoarseness | 85% | 3% |
| Globus cough etc. | 64% | 6% |
| pH-Monitoring |  |  |
| Total abnormal | 79% | 100% |
| Upright | 88% | 46% |
| Supine | 45% | 100% |
| Pharyngeal | 50% | 0% |
| Other Diagnostic Tests (Abnormal %) |  |  |
| Esophagoscopy & Bx | 27% | 100% |
| Barium swallow | 38% | 68% |
| Bernstein Test | 30% | 89% |
| Esophageal acid-clearance | 7% | 70% |
| UES manometry | 50% | 0% |
| H2-antagonist therapy |  |  |
| Failure rates | 35% | 10% |

Since patients with EEGR have predominantly upright, daytime reflux, while GERD patients appear to have supine, nocturnal reflux, it is not surprising that the esophageal acid clearance of patients with EEGR is almost always normal, while for esophagitis patients, it is almost always prolonged. These findings help explain why patients with EEGR do not have esophagitis. The total esophageal acid-contact time is normal in the EEGR group but not in the esophagitis group.

In addition to the lack of heartburn and esophagitis, patients with EEGR appear to have a very high rate of medical treatment failure with H2-receptor antagonists, regardless of dose. Koufman (1991) reported that the failure rate for patients with EEGR treated with ranitidine (in doses of 600 mg to 1,200 mg per day) was 38%. This rate of medical failure is more than double that of similarly treated GERD patients. The high rates of failure of treatment for EEGR with H2-antagonists may be due to three interrelated variables: (1) H2-antagonists reduce gastric acidity, but do not abolish it; (2) although it is generally accepted that pepsin activity is acid-activated, 70% of peptic activity still remains at a pH greater than pH 4.0 (Piper and Fenton 1965); and (3) it appears that the mucosa of the larynx is its sole protective barrier against peptic injury. If the mucosa is injured then ulceration, granulation and perichondritis may occur. This damage appears to be principally through exposure to pepsin in the refluxate (Koufman 1991; Little et al. 1985; Lillemoe et al. 1982; Hirschowitz 1991; Johnson and Harmon 1986; Samloff and Taggart 1987). Thus EEGR that affects the larynx could be termed "peptic laryngitis".

Reliable diagnostic tools for GERD, and in particular EEGR, have been sought for decades. Since the 1960s, pH-monitoring has been used to diagnose GER, because the acid in the refluxate is easily measured by pH monitoring. For this reason, double-probe pH monitoring was developed.

Double-probe pH monitoring is a technique which simultaneously measures the pH in the esophagus and throat by using a device that consists of dual pH sensors which are imbedded in a single catheter such that when placed in the throat and esophagus one probe is in the distal esophagus five centimeters above the LES and the other probe is in the hypopharynx behind the laryngeal inlet just above the UES. Patients are monitored for 24 hours. A precipitous drop below pH 4 in the pharyngeal probe which is immediately preceded by a comparable drop in pH in the esophageal probe is considered to be evidence of EEGR.

While this pH based assay appears to be the most sensitive and specific yet available for the diagnosis of EEGR, it has several disadvantages. Calculations of its sensitivity range from only 68% to 80% (Koufman 1991). Possibly because EEGR is an intermittent, "life-style-related" disease (Koufman 1991, 1996), a 24 hour monitoring period is not always sufficient to determine if a patient has been experiencing previous EEGR events or if future events may occur. This problem is exasperated by the nature of the assay, which detects hydrogen ions, a small molecule that does not persist in the throat. In addition, this technique is highly invasive, i.e. approximately 12% of otolaryngology patients either refuse or cannot tolerate the procedure. Furthermore, significant dietary modifications occur during the pH monitoring procedure, which may artificially suppress reflux, thus making a negative result questionable. And finally, the method is expensive and hence has limited availability.

Pepsin, considered to be acid-activated, has been ignored as a diagnostic marker of GERD and EEGR because acid (pH) is quite easy to measure compared to pepsin. But as patients with EEGR commonly do not have esophagitis, or heartburn, pH monitoring and other diagnostic assays, which test for esophagitis, are often falsely negative in these patients. Several immunoassays have been developed to measure the levels of pepsinogens I and II in serum and urine in order to evaluate their potential as diagnostic markers of either gastrointestinal ulcers or stomach cancer (Waldum et al., 1979; Axelsson et al., 1982; Huang et al., 1987; Huang et al., 1988). It is contemplated that pepsin may enter the blood serum through GERD induced lesions in the throat. However, changes in pepsin levels in either the blood serum or urine due to GERD have never been evaluated nor have they been contemplated for their use as diagnostic markers of GERD or EEGR.

There is an immediate need, therefore, for a noninvasive, accurate and less expensive diagnostic method which can be Used to diagnose EEGR and monitor the progress of treatments for a variety of disorders of the throat and esophagus that are EEGR and GERD related.

SUMMARY OF THE INVENTION

The present invention seeks to overcome certain deficiencies in the prior art by providing methods of detecting and diagnosing reflux diseases and disorders by detecting the presence of pepsin in airway secretions (e.g., throat, lung, esophagus, or mouth mucus/sputum/saliva) or other bodily fluids of subjects suspected of having a reflux disorder or disease. An advantage of the disclosed methods over methods based on detection of pH changes is that pepsin or pepsinogen from reflux becomes trapped in the mucus and remains in the throat or esophagus longer than acid (hydrogen ions) and can thus be detected for hours or days after a reflux event. Other advantages include the noninvasive nature and greater sensitivity of an immunoassay versus pH monitoring and the ability to detect neutral or weakly acidic reflux that may be missed by a pH monitoring method.

Gastric reflux was first associated with deleterious effects on the larynx (i.e. contact ulcer and granuloma of the larynx) by Cherry and Margulies (1968) and Delahunty and Cherry (1968). As used herein GER refers to a gastroesophageal reflux, or the presence of stomach contents in the esophagus. GER is composed of acid and pepsin. The term "GERD" as used herein means gastroesophageal reflux disease. Laryngopharyngeal reflux (LPR) is defined herein as the extraesophageal manifestation of GER and specifically refers to the backflow of gastric contents into the laryngopharynx (i.e. the throat). This term is interchangeable with the term "EEGR" but specifically applies to extraesophageal gastric reflux just into the laryngopharynx (i.e., the throat). Thus, although the two terms may be used interchangeably, the more general term is EEGR, but the term LPR has been used in the "laryngology literature." Herein, LPR and EEGR are used interchangeably.

All patients with LPR have some GER, but the reverse is not true (Koufman, 1991). In other words, for refluxed material to reach the throat, it must traverse the esophagus, but in most people with GERD, the refluxate never escapes the esophagus into the throat above, because the upper esophageal sphincter (UES) serves as an effective barrier to EEGR (Koufman 1991, Gerhardt et al. 1978, Kahrilas et al. 1987). As used herein, the abbreviation, LES refers to the lower esophageal sphincter, which separates the stomach from the esophagus. LPR is a clinically distinct disease from GERD.

The present invention may be defined in certain broad aspects as a method of detecting a gastric reflux comprising detecting pepsin or pepsinogen in the mouth, an esophageal or laryngeal area, an airway or bodily fluid sample (e.g. blood serum or urine) of a subject. The gastric reflux may be a manifestation of a gastroesophageal disease, a laryngopharyngeal reflux disease, or even a single acute condition or illness due to a dietary or lifestyle situation.

In certain preferred embodiments, the method of detecting is by immunoassay. The immunoassay may take any number of forms, including but not limited to an ELISA, a ELCA, a radioimmunoassay, immunoprecipitation, or other methods known in the art. Particularly preferred are those immunoassays in which an antibody is immobilized on a solid support. Such methods would include competitive ELISAs and would also include methods in which an immobilized antibody is attached to a sampling means such as a strip of paper, nitrocellulose or other suitable material, such that the antibody may be inserted into the mouth, throat and/or esophagus of a subject. In some embodiments, the immobilized antibody may be attached to an instrument or probe that is inserted into the throat for another purpose, such as an aspirator, an endoscope, a fiberscope, a laryngoscope, an endotracheal tube, a nasogastric tube, a pH catheter probe or other indwelling device.

Preferred antibodies for use in the present methods include any antibody that immunoreacts with the pepsins and pepsinogens found in the human stomach. Because the methods of the present invention do not depend on the ability to detect a particular isoform of pepsin or even of pepsinogen, a chicken antibody preparation is shown to be particularly effective due to its ability to crossreact with multiple antigens. However, antibodies from any source, such as rabbits, mice, rats, goats and even human cells are contemplated to be effective in the practice of the claimed methods.

In certain broad aspects, the present invention may be described as a method of diagnosing a gastric reflux disorder. This method comprises obtaining a sample from a subject suspected of having gastric reflux disorder, contacting the sample with an antibody immunoreactive with human pepsin and/or pepsinogen, detecting the immunoreaction and comparing the immunoreaction to a standard immunoreaction level. Once a standard for a particular population has been established, then one could compare the levels of pepsin or pepsinogen occurring in, for example, the mouth, the throat, the esophagus, or in secretions or fluids derived from such areas, of a member of that population group to diagnose a reflux disorder or event. Population groups might include, but would not be limited to adult males, adult females, or various ethnic groups. Borderline and pathogenic levels of pepsin may be established for any or all such groups in the practice of the claimed methods. In addition, knowledge provided by the present invention concerning the normal and pathological ranges of pepsin levels in infants, children and adults would establish the natural history of reflux-related diseases, and may be useful in the prediction and prognosis of the development of other airway conditions such as asthma, lung cancer and the sudden infant death syndrome, for example.

The sample to be analyzed may be an expectorate, a saliva sample, an airway mucosa sample or even a serum or urine sample. In certain embodiments the sample may be taken from the area between the lower esophageal sphincter and the upper esophageal sphincter of a subject, from the area above the upper esophageal sphincter of the subject, or both. The detection method may be based on a colorimetric label attached to the antibody, a fluorescent label attached to said antibody.

An aspect of the invention may be described in a broad embodiment as a kit for detecting a gastric reflux. The kit comprises an antibody immunoreactive with human pepsin or pepsinogen and a means for sampling a subject. The kit may also comprise labeling means, indicator reaction enzymes and substrates, and any solutions, buffers or other ingredients necessary for the immunoassay. Sampling means may include swabs, vials for expectorates or saliva samples or even strips impregnated with antibody. The components of the kit are contained in close confinement in a box, preferably of plastic or cardboard suitable for storing the kit in a refrigerator, freezer or shelf, when not in use. Also included may be pepsin or pepsinogen proteins to use as controls to establish a standard curve and written instructions detailing the protocols to follow in using the kits.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
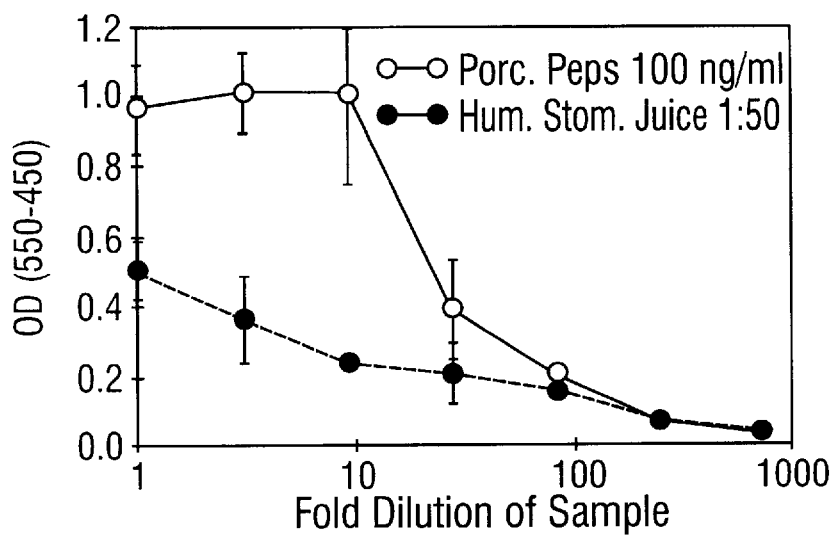
FIG. 1A. Results of ELISA-ELCA assays showing the ability of chicken antibodies to detect porcine and human pepsin in vitro.

It the discovery of the present inventor that a more effective, more sensitive, less expensive and less invasive test for EEGR is based on the immunodetection of pepsin, rather than the art accepted methods, which are based on detection of a low pH due to the presence of stomach acid. The present discovery is based on the knowledge that all GER contains pepsin, but not all reflux contains acid. For example, if a patient is treated with antacids, the patient may have neutral-pH reflux (reflux with a pH above pH 4) and still continue to suffer and develop any one of several diseases due to GER or EEGR. Therefore, the most important diagnostic component of gastric reflux to detect is not acid, or low pH which has been the accepted diagnostic marker by the medical community, but pepsin. In addition because pepsin is a large molecule which is not rapidly absorbed or neutralized, it can be detected in airway secretions much longer after gastric reflux occurs, compared to hydrogen ions (or low pH), because the pepsin is trapped in mucus and on mucosa by mucus producing glands. Hence an immunoassay based on the detection of pepsin has the potential to detect GERD and EEGR hours or days after a reflux event has occurred.

The present invention may be described in certain broad aspects as compositions and methods described herein which can be used to significantly improve the ability to diagnose and treat patients suffering from GERD, and especially from EEGR, by overcoming many of the disadvantages and limitations of current diagnostic methodology. The invention provides an easy to use, noninvasive diagnostic immunoassay with improved sensitivity and accuracy that is less expensive and less invasive than current diagnostic methods and consequently is expected to achieve greater acceptance by the medical community.

Specifically, the invention may be described in certain embodiments as an ultra-sensitive, highly specific immunoassay which is capable of detecting human pepsin in vitro and in vivo (e.g. in airway secretions), particularly in throat sputum. Pepsin is always present in gastric-content reflux and its presence in throat sputum is considered evidence of LPR. Because the presence of any isoform of pepsin is diagnostic for LPR, it is not necessary to differentiate between the different isoforms of human pepsin or between acid-activated and inactive (pepsinogens) forms of pepsin. Hence this invention has the added advantage of being able to diagnose LPR in the neutral pH reflux of patients that are on acid-suppressive therapy which current methodology cannot.

The anti-porcine pepsin antibodies disclosed herein may be used to purify human pepsin from gastric fluid or autopsy stomach extracts for use as a specific antigen for further antibody production. Because cross-reactive determinants are detected in the practice of the present invention, the same chickens may be "boosted" with the human antigen to produce additional cross-reactive antibodies for use in the methods disclosed herein. These anti-human antibodies from the "boosted" chickens are contemplated to have even greater sensitivity for use in diagnosis of GER, and in particular EEGR, as described herein.

The approach developed for this assay was based on a known general relationship between evolutionary divergence and immunological recognition. In general, the more ancient the evolutionary divergence between species from a line of common ancestry then the greater the immunological recognition and cross-reactivity between the species. For example, antibodies are raised against mammalian IgG in both mammals and chickens. The anti-mammalian IgG antibodies raised in chickens will recognize the IgGs of evolutionarily widely divergent mammalian species; whereas, the anti-mammalian IgG antibodies raised in mammals will principally recognized only the IgG of that specific antigen and of mammalian species which are evolutionarily, closely related to the immunized mammalian species (Neoh et al. 1973).

The point of mammalian species divergence from avian species was several hundred million years ago, therefore, if there are any common structural features which differentiate mammalian pepsins from avian pepsins, it is likely that chicken antibodies would be able to recognize these determinants. Based on this assumption, antibodies from chickens that were immunized with porcine pepsin should be able to cross-react with human pepsins to be used to detect the presence of pepsin in throat sputum or other human samples.

The antibodies and methods and methods developed as a part of the present discovery are also useful to quantitate normal levels of pepsins and pepsinogens in the esophagus and throat areas of a general population, or even in the serum and urine of a general population. The knowledge of normal levels will be useful in diagnosis and prognosis of gastric reflux disorders by any means that depends on determining pepsin levels in any biological sample. The anti-porcine pepsin antibodies are also useful to isolate human pepsins and pepsinogens through cross-reactivity, and those human proteins are useful to develop more human-specific antibodies for use in the disclosed methods. It is contemplated that these anti-human pepsin antibodies are more sensitive in the practice of the claimed methods.

It is understood that the pepsin immunoassays for detection of gastric reflux as disclosed herein may replace the pH based methods of the prior art. Of particular advantage is the increased sensitivity, the longer period after a reflux event in which pepsin may remain compared to acid, and the ability to simplify the assay into a solid support format, e.g. a dipstick. However, it is also contemplated that these novel methods may be used in conjunction with a pH based method to provide a second method of diagnosis, and a means for sampling for the immunoassay may even be attached to a pH probe for simultaneous sampling by both methods.

Immunodetection Methods

In certain embodiments, the present invention concerns immunodetection methods for binding, purifying, removing, quantifying or otherwise generally detecting pepsin. The methods of the present invention may be employed to detect pepsin proteins or peptides. The steps of various useful immunodetection methods have been described in the scientific literature, such as, e.g., Nakamura et aL (1987), incorporated herein by reference.

In general, the immunobinding methods include obtaining a sample suspected of containing pepsin proteins, peptides or anti-pepsin antibodies and contacting the sample with an antibody or pepsin protein or peptide in accordance with the present invention, as the case may be, under conditions effective to allow the formation of immunocomplexes.

In terms of antigen detection, the biological sample analyzed may be any sample that is suspected of containing pepsin proteins or peptides, such as saliva, throat sputum, GER, mucosa, mucosa preparations, a mucosal membrane, a mucosal membrane preparation, separated or purified forms of any of the above protein-containing compositions, or even any biological fluid that comes into contact with the aforementioned tissues, such as, blood serum or urine.

Contacting the chosen biological sample with the antibody under conditions effective and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound proteins or peptides, allowing only those proteins or peptides specifically bound within the primary immune complexes to be detected.

In general, the detection of immunocomplex formation is well known in the art and may be achieved through the application of numerous approaches. These methods are generally based upon the detection of a label or marker, such as any of the radioactive, fluorescent, biological or enzymatic tags or labels well known to those skilled in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Immunoassays

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and other solid support immunoassays known in the art. Most preferred are ELISAs as described by Doellgast et al. (1993, 1994) and by U.S. Pat. No. 4,668,621. Immunohistochemical detection using tissue sections and radioimmunoassays (RIA) are also particularly useful. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a biological sample suspected of containing the pepsin or pepsinogen antigen(s), which may itself be linked to a detectable label, is added to the wells. After binding and washing to remove non-specifically bound immunecomplexes, the amount of bound pepsin or pepsinogen antigen(s) may be determined.

Alternatively, the first added component that becomes bound within the primary immune complexes may be detected by means of a second binding ligand that has binding affinity for the primary antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound, labeled secondary antibodies or ligands, and the remaining label in the secondary immune complexes is then detected. This type of ELISA is a simple "sandwich ELISA".

Further methods include the detection of primary immune complexes by a two step approach. A second binding ligand, such as an antibody, that has binding affinity for the primary antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

In another exemplary ELISA, the samples suspected of containing the pepsin or pepsinogen antigen(s) are immobilized onto the well surface and then contacted with antibodies of the invention. After binding and washing to remove non-specifically bound immunecomplexes, the bound pepsin or pepsinogen antigen(s) are detected. Where the initial antibodies are linked to a detectable label, the immunecomplexes may be detected directly. Again, the immunecomplexes may be detected using a second antibody that has binding affinity for the first anti-pepsin or pepsinogen antibody(ies), with the second antibody being linked to a detectable label.

Another ELISA in which the proteins or peptides are immobilized, involves the use of antibody competition in the detection. In this ELISA, labeled antibodies are added to the wells, allowed to bind, and detected by means of their label. The amount of pepsin or pepsinogen antigen(s) in an unknown sample is then determined by mixing the sample with the labeled antibodies before or during incubation with coated wells. The presence of pepsin or pepsinogen antigen(s) in the sample acts to reduce the amount of anti-pepsin or pepsinogen antibody(ies) available for binding to the well and thus reduces the ultimate signal.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with non-reactive material to reduce background, and washing to remove unbound material, the immobilizing surface is contacted with the control antigen and/or biological sample to be tested under conditions in a manner conducive to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions in a manner conducive to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

The use of the methods and compositions disclosed herein are not limited to those technologies known in the art such as ELCA, ELISA plate, dot blot, western blot or other assays which use solid supports as part of their methodology. The present invention may also be integrated with other devices or methods for the diagnosis or monitoring of gastric reflux. These other devices may include but are not limited to pH catheter probes, double pH probe devices, endoscopes, fiberscopes, laryngoscopes, nasogastric tubes, endotracheal tubes or other devices to which primary, secondary or tertiary immune complexes may be bound such that pepsin proteins or peptides may be detected. In addition, monitoring ports may be placed in endotracheal tubes that are indwelling for anesthesia (for surgery) or for life support in critically ill patients.

Alternately, "pepsin-assay-impregnated test-strips" may be imbedded in endotracheal tubes for a one-time measurement of pepsin in the airway secretions. Similar devices for use in the nasopharynx and throat are also contemplated as part of sleep monitoring procedures and for reflux-screening of other specific patient groups. It is also understood that samples may be taken from more than one location in the esophagus and throat, for example, and quantitatively compared in order to more accurately diagnose EEGR. In addition these "pepsin-assay-impregnated test-strips" may be combined with a pH test-strip and/or other markers for inflammation to aid in the detection of EEGR or other associated conditions.

A "pepsin-assay-impregnated test-strip" preferably comprises an antipepsin or antipepsinogen antibody bound to the test-strip material. When this strip contacts pepsin in a sample from a patient, a pepsin/antibody complex is formed. After washing, this complex is detected by a second or even a third antibody conjugated to an indicator moeity as discussed above.

Antibody Generation

Means for preparing and characterizing antibodies are well known in the art (See, e.g. Antibodies: A Laboratory Manual, Cold Spring Harbor Laboratory, 1988; incorporated herein by reference).

Polyclonal Antibodies

Briefly, a polyclonal antibody is prepared by immunizing an animal with an immunogenic composition in accordance with the present invention (either with or without prior immunotolerizing, depending on the antigen composition and protocol being employed) and collecting antisera from that immunized animal. A wide range of animal species can be used for the production of antisera. Typically the animal used for production of anti-antisera is a rabbit, a mouse, a rat, a hamster, a guinea pig, a chicken or a goat. Because of the relatively large evolutionary divergence between avian species and mammalian species, a chicken is a preferred choice for production of polyclonal antibodies to mammalian pepsins.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (13SA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies (MAbs).

Monoclonal antibodies

Because the methods of the present invention are contemplated to be more effective if any pepsin or pepsinogen occurring in the stomach is recognized by the immunoassays, a certain amount of cross-reactivity is desired. Therefore, polyclonal antibodies that recognize as many pepsin or pepsinogen antigens as possible are preferred. Alternatively, one may use a mixture of monoclonal antibodies, each directed to a particular pepsin or pepsinogen.

The methods for generating MAbs generally begin along the same lines as those for preparing polyclonal antibodies. MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified pepsin protein, polypeptide or peptide (or any protein complex, such as a fusion protein containing an immunologically active portion of the a pepsin protein, if used after tolerization to common antigens). The immunizing composition is administered in a manner effective to stimulate antibody producing cells. Chickens are preferred animals, however, the use of rat, murine, rabbit, sheep or frog cells is also possible.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, OF, NSOIU, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al.(1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

EXPERIMENTAL PROCEDURES

Immunization of goats and chickens

Five mg of pure porcine pepsin (Sigma Chemicals, St. Louis, Mo.) in a dried tube was dissolved and emulsified in complete Freund's adjuvant and injected subcutaneously into 1 goat or 3 chickens. Booster injections of the same amount in incomplete Freund's adjuvant were injected at monthly intervals thereafter. Blood samples were obtained at monthly intervals from all animals, and the eggs were collected daily starting from the time of immunization.

Preparation of chicken IgY fraction

Chicken antibodies were prepared as described by Doellgast et al. (1994). Yolks were separated from eggs and suspended in 0.025M potassium phosphate-buffered saline, pH 7.6 (2 ml per ml of yolk). Polyethylene glycol (mol wt 8000) was added to a concentration of 3%, and the resulting suspension was centrifuged at 5,000 g for 30 minutes. Polyethylene glycol was added to a final concentration of 12%, and the suspension was again centrifuged to obtain the IgY-containing pellet. This IgY-containing pellet was dissolved in 0.02M potassium phosphate buffer, pH 7.6, centrifuged at 12,000 g for 10 minutes to remove particulates and bound to a column of QAE-agarose (Q-Sepharose, Pharmacia Fine Chemicals, Picataway, N.J.). A gradient of 0.0 to 0.3M NaCl was used to separate an IgY fraction, which eluted with a peak at approximately 0.15 SM NaCl. The fraction was precipitated with 40% saturated ammonium sulfate, dialyzed against phosphate-buffered saline, and either brought to 50% glycerol concentration or used in this form for immunoabsorption.

Preparation of goat Ig fraction

Goat serum was brought to an ammonium sulfate concentration of 40% saturation by addition of 240 g of ammonium sulfate per liter of serum and pelleted by centrifugation. This pellet was dialyzed against 0.05 M potassium phosphate, 0.15 M sodium chloride, pH 7.6, and either brought to 50% glycerol concentration or used in this form.

Preparation of pepsin immunoabsorbents

3M Corporation Emphasem™ (Pierce Chemicals, Rockford, Ill.) absorbent was mixed with pepsin dissolved in 1M potassium phosphate, pH 7.6, at a ratio of 40 mg pepsin per gram of Emphase™ suspended in 2×the rehydration volume of Emphase™ (approx 6 ml per gram). The mixture was allowed to incubate overnight at room temperature with mixing and was then poured into a 1 cm×10 cm glass column. The column was blocked with 1M Tris-Cl, pH 8.5, washed with PBS extensively, then treated with 4M NaCl in 0.05M imidazole-HCl buffer, pH 8.0, and then with 4M $MgCl_2$ in 0.05M imidazole-HCl, pH 8.0. The column was then washed with 0.05 M imidazole-HCl, 0.15 M NaCl, pH 7.8, and used for immunoabsorption.

Immunoabsorption purification of specific antibodies

Antibody fractions from either chicken or goat sources were passed through the pepsin column and washed with IM NaCl in 0.05M imidazole-HCl, pH 8.0. After about 5 column volumes of wash, the bound antibody was eluted with 4M $MgCl_2$ in 0.05M imidazole-HCl, pH 8.0, as described previously for purification of RVV-XA from snake venom (Durkee et al. 1993). Fractions containing the eluted antibody were concentrated in an Amicon (Beverly, Mass.) apparatus equipped with a YM-10 membrane and were repeatedly concentrated after being dissolved in 0.05 M imidazole-HCl buffer, pH 8.0. The antibody was precipitated using 40% saturated ammonium sulfate and applied to a 1×50 cm column of Sephacryl S 200™ (Pharmacia Fine Chemicals) in order to separate the IgG (goat) or IgY fraction (chicken) from the aggregated material, immune complexes and IgM (goat) appearing in the void volume. Fractions were pooled from the retained immunoglobulin peak, concentrated by precipitation, using 40% saturated ammonium sulfate, dialyzed and brought to 50% glycerol by dialysis against an equal volume of 100% glycerol with mixing overnight at room temperature.

Preparation of conjugates

Immunoglobulins in 0.1 M potassium phosphate, pH 7.6, were treated with 5mM dithiothreitol for 30 minutes at 37° C. The reduced immunoglobulins were separated on a spin column of SEPHADEX G25 equilibrated with 0.1M potassium phosphate, pH 7.6. The void volume containing 1 mg of reduced immunoglobulin was mixed with 1 mg of a 20 mg/ml solution of RVV-XA-SMCC (as described previously by Doellgast (1987)) or with a 5OmM solution of fluorescein maleimide to a final concentration of I mM. The RVV-XA-conjugate was allowed to react at room temperature for 4–16 hours, and the fluorescein-maleimide-conjugate for 1 hour. The fluorescein maleimide was rapidly separated from the fluorescein-labeled immunoglobulin on a spin column of G-25 SEPHADEX. The RVV-XA-Ig conjugate was used without further purification.

Performance of ELISA-ELCA assays; cross-reactivity of porcine and human pepsin

ELISA-ELCA assays are performed as described by Doellgast et al. (1994) and Doellgast et al. (1993). Plates coated with either 10 µg/ml of affinity-purified goat or chicken antibody in 0.2M sodium bicarbonate, pH 9.5, are mixed with either porcine pepsin standard or fluid ("human stomach juice") aspirated from the stomach of a volunteer using a nasogastric tube and neutralized using IM dipotassium phosphate buffer to a pH of 7.6. Samples are diluted in 50 mg/ml casein, 0.05M imidazole-HCl, pH 8.,0, containing 0.5 % Triton X-100. Incubation is for 1 hour at 37° C. or overnight at 4° C. The plate is then washed and RVV-XA (Russell's viper venom coagulation activating enzyme)-antibody is added and the plate is incubated for 30 minutes at 37° C. The plate is washed and Elcatech kits (Elcatech Inc., Winston-Salem, N.C.) for measurement of bound RVV-XA are used to measure the bound conjugate as described by the manufacturer.

Separation of pepsin from gastric juice

Using the antibody preparation which binds pepsin, pepsin reactive with this antibody is purified on antibody columns. Gastric juice obtained through a nasogastric tube inserted into volunteers is neutralized, filtered and passed through a column of antibody. Immunoreactive material is monitored using the pepsin-specific assay, and this material binds to the column and is eluted using 4M $MgCl_2$. The eluted protein is further characterized using electrophoresis, ion exchange and isoelectric focusing separation. Immunoassay and pepsin activity assays are used to routinely evaluate these separated fractions. Since there are several isotypes of human pepsin, i.e. several protein isotypes, variations in specific reactivity for separated components can occur. Fractionation of the gastric juice without immunoabsorption and assay of both pepsin activity and immunoreactivity are used to determine which if any isotypes are not reactive with the anti-porcine antibodies.

Preparation of antibodies against human pepsin

The human pepsin which is immunoabsorbently purified and chromatographically separated as described is used to raise antibodies in chickens and goats which are more specifically reactive with human pepsin compared to those antibodies raised against porcine pepsin. These antibodies are purified on columns of human pepsin or on the same columns of porcine pepsin which were previously used to purify chicken antibodies. These newly purified antibodies have even greater affinity for the homologous human pepsin than those antibodies raised against the heterologous porcine pepsin. Selection in favor of high affinity anti-human pepsin antibodies is also expected.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Detection of mammalian pepsins in vitro

Antibodies raised against porcine pepsin in both chickens and goats were examined for their ability to cross-react with and detect human and porcine pepsins. ELISA-ELCA assays were performed and all materials were prepared as described herein.

Figure 1B:
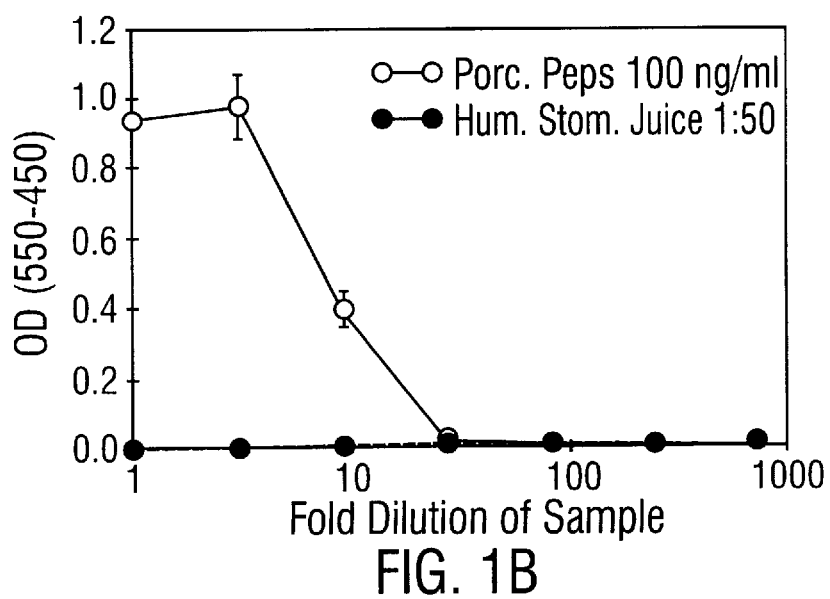
FIG. 1B. Results of ELISA-ELCA assays showing the ability of goat antibodies to detect porcine pepsin in vitro.

Chicken antibodies show strong cross-reactivity to both human and porcine pepsin (FIG. 1A); whereas, goat antibodies show only modest cross-reaction to porcine pepsin and no cross-reaction to human pepsin (FIG. 1B). Porcine pepsin was reliably detected to a level of 1 ng/ml by the chicken antibodies. As the concentration of pepsin in "human stomach juice" was not determined, the level of detection for human pepsin could not determined. The assay was also able to detect both active (porcine) and inactive (human) forms of pepsin, which is ideal for detecting LPR in patients with persistent, neutral-pH reflux.

EXAMPLE 2

Quantitative detection of porcine pepsin over time in vivo in a rat model

Antibodies raised against porcine pepsin in goats were used to measure porcine pepsin in rat throat/sputum samples after the rats ingested porcine pepsin. Throat/sputum samples were taken immediately after instillation and periodically thereafter for 5 hours. Samples were obtained by laryngeal washing. ELISA-ELCA assays were performed and all materials were prepared as described herein.

Figure 2:
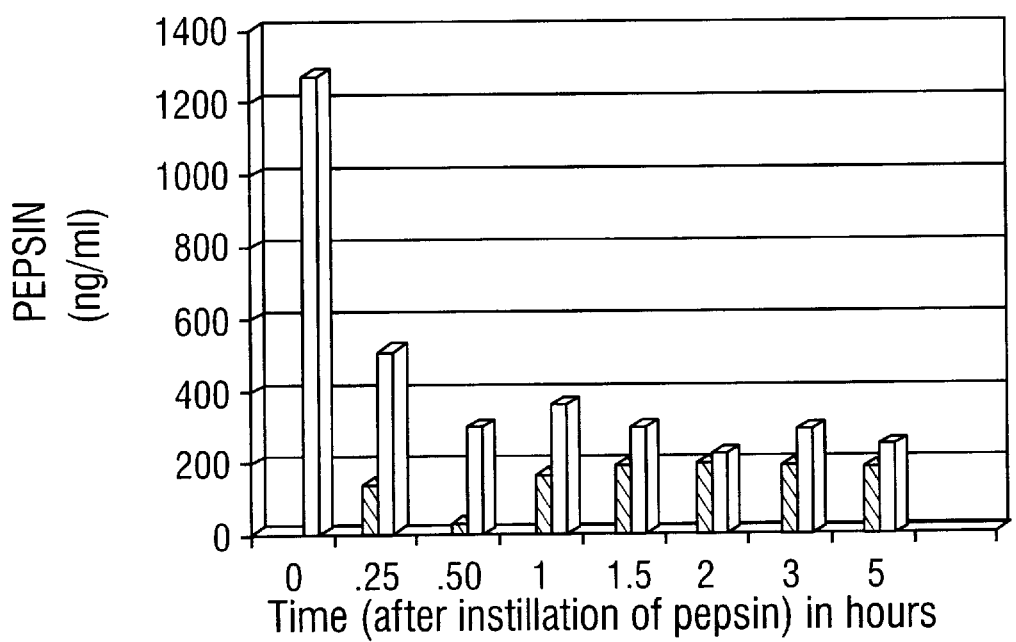
FIG. 2. Quantitative detection of porcine pepsin, by goat antibodies, for up to five hours following a single, artificially induced pharyngeal reflux episode. Bars represent two replicates obtained from laryngeal washings of rats.

Studies were performed in duplicate, and the amount of porcine pepsin detected in the laryngeal washings after instillation of 200 µg of porcine pepsin (time equals zero) to five hours post instillation for each replicate are shown in FIG. 2. After a single application to the rat throat, pepsin was effectively detected in the 100–500 ng/ml range for up to 5 hours after an artificially induced reflux episode. These results demonstrate that pepsin can be used as a diagnostic marker for reflux events and is measurable in tissue secretions for several hours after a single reflux event.

EXAMPLE 3

Quantitative detection of porcine pepsin over time in vivo in a human

In a similar study, antibodies raised against porcine pepsin in goats were used to measure porcine pepsin in human throat/sputum samples. Porcine pepsin was instilled into the throat of a normal, i.e. without history of reflux, volunteer through a nasogastric tube; 200 μg of pepsin were instilled in 1 ml of saline, adjusted to pH 3.0. Samples were taken immediately after instillation and periodically thereafter for 2 hours. Aliquots of throat/sputum were obtained by the subject clearing the throat and spitting into a sample holder. ELISA-ELCA assays were performed and all materials were prepared as described herein. Results are shown in Table 2. These results show that pepsin is measurable in human throat secretions for at least two hours after it is introduced into tissue and demonstrates that pepsin can be used as diagnostic marker for reflux events in humans. Note, control values obtained prior to instillation were negative but are set to "zero" in Table 2 for ease of presentation.

TABLE 2

Detection of porcine pepsin (ng/ml) in human throat/sputum over time.

| | time post instillation (in hours) | | | | | |
|---|---|---|---|---|---|---|
| Prior to instillation | 0* | .25 | .50 | 1.0 | 1.5 | 2.0 |
| 0** | 1186 | 220 | 162 | 74 | 54 | 62 |

*Sample taken immediately after instillation designated as time zero (0).
**ng/ml of porcine pepsin detected

EXAMPLE 4

Detection of human pepsin in vivo; correlation with incidence of LPR

Antibodies raised against porcine pepsin in chickens were examined for their ability to cross-react with and detect human pepsins in human sputum. ELISA-ELCA assays were performed and all materials were prepared as described herein. Results of clinical studies with eleven subjects who were asked to "clear your throat and spit into a test-tube." are shown in Table 3.

TABLE 3

Results of clinical studies with the pepsin immunoassay

| SUBJECT# | CLINICAL HISTORY | ASSAY RESULT | SMOKER |
|---|---|---|---|
| J01 | May have LPR* | + | Yes |
| J02 | pH-documented LPR* | +++ | No |
| J03 | on Prilosec | neg. | No |
| J04 | LPR-induced stenosis | + | No |
| J05 | | + | No |
| J06 | | neg. | No |
| J07 | Probable (undocumented) LPR* | +++ | No |
| J08 | | neg. | Yes |
| J09 | Probable (undocumented) LPR* | + | No |
| J10 | May have LPR* | ++ | Yes |
| J11 | Probable (undocumented) LPR* | ++ | Yes |

*Patient exhibited symptoms of hoarseness, globus, dysphagia, chronic throat clearing, and/or cough.

Of the eleven people examined, 73% (8 of 11) had pepsin found in their expectorates. The subjects with LPR had higher levels of pepsin than the other pepsin-positive subjects. Based upon the reported symptoms of the latter subjects, some of them may have LPR. These results were not quantified more precisely as the "normal" range for pepsin in human sputum/throat expectorate has not yet been established. However, the findings indicate that a "normal" range, a "borderline" range, and a "definitely abnormal" range for human pepsin can be determined with this assay. It is possible that this determination will involve taking multiple samples from individuals over time in order to establish these ranges. The normal, borderline and definitely abnormal ranges are to be used to develop a standardized assay to routinely detect human pepsin appearing in saliva due to reflux episodes. Certain embodiments may include a kit for the routine measurement of pepsin in clinical situations using a solid support, such as a "dipstick".

EXAMPLE 5

Clinical Trials in an Asymptomatic Population

In order to establish normal clinical parameters for the pepsin assay in humans, clinical trials, using a large (N=300) community-based human population, which is grouped according to reported symptomatology, are conducted. These data also yield information about the prevalence of LPR symptoms.

The specific aims of an exemplary clinical studies outlined in this and the following examples are as follows:

(1) To develop "normal" ranges for pepsin levels in throat sputum from a cohort of individuals selected as being asymptomatic for LPR;

(2) Within this cohort, examine the pepsin and pH levels of participants who are and are not clinically disposed for LPR, based on a profile of lifestyle and history measure that have been developed;

(3) Describe associations that individual lifestyle, history and demographic (including gender, age, and ethnicity) components have with pepsin and pH levels in an asymptomatic cohort;

(4) Characterize the agreement between measures from pH and pepsin monitoring in an asymptomatic cohort;

(5) Characterize the associations between lifestyle, history and demographic factors; pepsin levels; pH levels; symptoms; and disease status across all study cohorts (see Examples 6 and 7). Each cohort is expected to include specific subgroups (i.e. defined by gender, age, ethnicity, lifestyle, history, and disease severity). All are aged 20–69 years and will have provided informed consent. Three representative cohorts of participants are accessed: asymptomatic normals; patients with laryngeal disease; and patients with pulmonary and respiratory diseases.

Since there are no well-established standards that completely rule-out or rule-in the diagnosis of LPR, the invention is used to sample the general population and establish a "normal range" for pepsin. This is important for four reasons: (1) to establish the prevalence of LPR symptomatology in a cohort of volunteers; (2) to establish the range of pepsin assay values and pH levels; (3) to correlate LPR with lifestyle and other relevant variables; and (4) to define different subgroups within the control group cohort based on reported symptoms and pepsin and pH levels.

LPR symptoms are reported by most patients with LPR, and presumably people who do not have LPR will rarely report its symptoms. Previous investigations with 20 normal (i.e. asymptomatic for LPR) human volunteers with double-probe pH monitoring found none to have any pH-documented LPR; therefore, it is likely that investigation of a group of totally asymptomatic control subjects might reveal very infrequent LPR, and pepsin values of zero. Consequently, evaluation of two groups of subjects within the community-based cohort may be done, with responses to the "LPR Symptom Questionnaire" (LSQ) determining the subjects' group. The LSQ includes the following groups of variables:

Demographic information (e.g., age, gender, race)

Past medical history (e.g., "reflux-related" conditions and medications)

Lifestyle history (e.g., tobacco and alcohol use)

LPR symptoms (e.g., hoarseness, globus, dysphagia, heartburn)

Morphologic information (i.e., subjects' height and weight Within the LSQ are seven questions (#13–#19) about LPR symptoms, shown here:

(13) How often, if ever, do you have heartburn or stomach acid coming up in a week? 1. Never 2. Rarely 3. A few times per week 4. Daily 5. Most of the time

(14) How often, if ever, do you have a sensation of a lump in the throat in a week? 1. Never 2. Rarely 3. A few times per week 4. Daily 5. Most of the time

(15) How often, if ever, do you have frequent throat clearing or too much throat mucus? 1. Never 2. Rarely 3. A few times per week 4. Daily 5. Most of the time

(16) How often, if ever, do you have a difficulty swallowing or food sticking? 1. Never 2. Rarely 3. A few times per week 4. Daily 5. Most of the time

(17) How often, if ever, do you have choking episodes (average per week)? 1. Never 2. Rarely 3. A few times per week 4. Daily 5. Most of the time

(18) How often, if ever, do you have a nagging cough? 1. Never 2. Rarely 3. Afewtimesper4. Often 5. Most of the time

(19) How often, if ever, do you have hoarseness or a problem with your voice? 1. Never 2. Rarely 3. A few times per year 4. Often 5. Most of the time Analyses of pilot data from 64 volunteers indicate that summing the ranked responses to these questions has internal validity. Principal components analyses indicate that the major source of variation among these volunteers was defined by a rough sum of these ranks (a linear combination with nearly uniform loads): this component explained 23% of the total variation.

Using the numbered codes to the left of each response, one can see that the lowest possible score, for a completely asymptomatic person, would be 7, and that the highest possible score, for a symptomatic person, would be 35. In addition, subjects are specifically asked (question # 7) if they have "reflux/hiatal hernia/esophagitis." The responses to questions #7 and #13 through #19 form the basis for assignment of volunteers into the two control-groups: Group 1.1 - - - Asymptomatic "normal" group - - - and Group 1.2 - - - "Subclinical" (some reflux symptoms) group.

Results of preliminary testing of the LSQ with 41 Otolaryngology clinic patients with "ear diseases" (N=20) and with "LPR" (N=21), are shown in Table 4.

TABLE 4

LSQ scores for patients with either "ear diseases" or LPR

| "EAR DISEASE" GROUP | | LPR GROUP | |
|---|---|---|---|
| LSQ Score | # Subjects | LSQ Score | # Subjects |
| 7 | 3* | 11 | 3 |
| 9 | 3* | 13 | 1 |
| 10 | 1* | 15 | 1 |
| 11 | 3 | 18 | 2 |
| 13 | 1 | 19 | 1 |
| 14 | 3 | 20 | 3 |
| 16 | 2 | 22 | 2 |

TABLE 4-continued

LSQ scores for patients with either "ear diseases" or LPR

| "EAR DISEASE" GROUP | | LPR GROUP | |
|---|---|---|---|
| LSQ Score | # Subjects | LSQ Score | # Subjects |
| 17 | 2 | 23 | 3 |
| 18 | 2 | 24 | 1 |
|  |  | 25 | 1 |
|  |  | 26 | 1 |
|  |  | 29 | 1 |
|  |  | 31 | 1 |

*Subjects with scores of 10 or less would be normal controls (Group 1.1)

Thus, of the 20 ear patients, 35% (7/20) would satisfy the criteria to be included in Group 1.1, and 65% (13/20) would qualify to be in the "subclinical LPR" group, i.e., Group 1.2, and obviously, none of respondents in the LPR group would qualify as controls.

Sampling and Inclusion and Exclusion Criteria

Community-based "normal" controls are accessed by newspaper solicitation. This method of accessing participants may not provide a sample that is fully representative of the community, due to selection biases typical among volunteers for medical studies and media-based solicitation, however a completely random sample would involve considerable expense. To provide an assessment of the appropriateness of the study sample, demographic characteristics of the sample are compared with those of the general population.

Respondents are asked to complete an LSQ and return it to the Voice Center by mail. Only individuals who return fully completed questionnaires are invited to participate in the study. Equal numbers of women and men, and equal numbers of participants in each of the five decades within the designated age range are recruited to allow efficient characterizations across these factors. The target population is 30% African-American and 65% Caucasian, which reflects roughly the demographic make-up of Forsyth County, N.C. Approximately 35% of adults in the geographical area smoke cigarettes.

The community-based sample will segregate into two subgroups according to reported symptomatology:

Group 1.1 - - - Asymptomatic "Normal" Control Group Inclusion Criteria:

Group 1.1 subjects must have LSQ symptom scores of 10 or less, and they must be able to tolerate the entire pH study, and have accurately completed the diary that accompanies the pH study. In addition, they must be able to produce and collect the required throat/sputum samples for pepsin assay.

Exclusion Criteria:

Group 1.1 subjects must not have self-reported "reflux, hiatal hernia, or esophagitis"(i.e., they must not have checked the "reflux box" in LSQ question #7). In addition, respondents who indicate that they cannot produce any throat mucus (LSQ #24) are excluded.

Group 1.2—"Subclinical" Group Inclusion Criteria:

Group 1.2 subjects may have LSQ symptom scores of more than 10, and they must be able to tolerate the entire pH study, and have accurately completed the diary that accompanies the pH study. In addition, they must be able to produce and collect the required throat/sputum samples for pepsin assay.

Exclusion Criteria:

Group 1.2 subjects must not have self-reported "reflux, hiatal hernia, or esophagitis" (i.e., they must not have checked the "reflux box" in LSQ question #7). In addition, respondents who indicate that they cannot produce any throat mucus (LSQ #24) are excluded.

Experimental Protocol

Subjects who meet the criteria for inclusion in Groups 1.1 and 1.2 of this study are enlisted after they have read and signed the Institutional-Review-Board-approved "Informed Consent" and the study agreement. The study coordinator reviews their responses to the LSQ with individuals to ensure all questions are understood and to enhance accuracy. After an overnight fast, each subject is seen in the pH laboratory. All aspects of the study are explained in fall to each subject by the Project Administrator or the pH technician. Before leaving the pH laboratory, each subject is given a "pH-study diary sheet" and labeled throat sputum collection tubes.

Sampling of Throat Sputum for Pepsin Assay:

Each subject receives a set of ten (10) numbered vials that are labeled with the subjects own name and the date of the study. Each subject is asked to supply sputum samples for pepsin assay at the following times:

(1) Prior to esophageal manometry and placement of the pH probes This sample is obtained to provide a baseline pepsin value during fasting, and so that the patient can be supervised in how to collect the sputum samples.

(2) Just after placement of the pH probes This sample is obtained to assess the effects of placement of the pH monitoring device, and to assess the sensitivity of the pepsin assay. Since with manometry and pH-probe placement, tubes are placed into the stomach and then withdrawn into the pharynx, it is likely that gastric juices are deposited on to the pharyngeal mucosa in minute quantities as a result of these procedures. This is also a second supervised sample.

(3) Prior to the first meal (breakfast or lunch) after pH-probe placement This sample is obtained to provide a second data point, a baseline value, during fasting.

(4) One hour after the first meal (breakfast or lunch) This sample is obtained to assess LPR in the post-cibal period.

(5) Prior to the evening meal This sample is obtained to provide a third data point in a semi-fasting state.

(6) One hour after the evening meal This sample is obtained to assess LPR in the post-prandial period. Previous pH data indicate that the post-prandial period is the most common time for LPR to occur in patients with LPR.

(7) Prior to bed This sample is obtained to provide a point for comparison with sample #8.

(8) First thing in the morning, after rising This sample is obtained to provide information about the supine nocturnal period, and it is another fasting data point.

(9) One hour after breakfast This sample is obtained to assess LPR in the post-cibal AM period.

(10) Just prior to removal of the pH probe This is another supervised sample that is obtained as an "ending" pepsin level.

Subjects are asked to record the time that each sample is obtained in two ways: by writing the time of sampling on the pH diary, and by pushing a button on the pH monitor that records the event on the pH study tracing. (This button is called "an event marker.")

Esophageal Manometry and pH Monitoring

All subjects also have esophageal manometry and double-probe pH-testing performed according to the standard protocol for this method. Since the techniques have been reported, (Koufman, 1991; Richter, 1991; Koufman et al., 1988; Koufman, 1993; Koufman, 1996; Weiner et al., 1987; Weiner et al., 1989) and since the technique is standard, (Koufman, 1991; Richter, 1991; Richter et al., 1992) the specifics are not repeated herein.

EXAMPLE 6

Clinical Trials in Patients with Laryngeal Diseases

The specific aims of the clinical studies outlined in this and the following example are as follows:

(1) By accessing separate symptomatic cohorts, examine ranges of pepsin and pH levels among participants with laryngeal disease (laryngeal edema, benign laryngeal lesions, and malignant/pre-malignant laryngeal lesions);

(2) Examine the impact of disease type and severity on pepsin and pH levels.

At present, clinicians at the Voice Center annually diagnose and treat hundreds of patients with "reflux laryngitis" and LPR-related benign and malignant vocal fold lesions. From this group, a cohort of study subjects is randomly selected with the following breakdown: Group 2.1 - - - No lesions LPR group (i.e., "reflux laryngitis" without any mucosal lesions) and Group 2.2 - - - Laryngeal lesion group (e.g., vocal nodules, cysts, polyps, carcinoma).

Sampling and Inclusion/Exclusion Criteria

Lists of patients seen by attending physicians at the Voice Clinic are generated and patients aged 20–70 years who meet the inclusion/exclusion criteria below are randomly sampled and solicited for entry into the study. The study coordinator telephones these prospective participants, briefly describes the study, and mails a LSQ to those who express interest. Prospective participants who return completed questionnaires are invited to visit the Voice Clinic to enroll in the study. These visits include a full description of the study and obtaining informed consent from each participant.

Group 2.1 - - - "No Lesion" LPR Group (N=50) Inclusion Criteria:

To be included, the subject must have pH-documented LPR, but no laryngeal "lesions." The subject must be able to tolerate the entire pH study, and have accurately completed the diary that accompanies the pH study. In addition, they must be able to produce and collect the required throat/sputum samples for pepsin assay.

Exclusion Criteria:

Group 2.1 subjects must not any have inflammatory or neoplastic lesions of the larynx. In addition, respondents who indicate that they cannot produce any throat mucus (LSQ #24) are excluded.

Group 2.2 - - - "Laryngeal Lesions" LPR Group (N=50) Inclusion Criteria:

To be included, the subject must have pH-documented LPR, and one or more laryngeal lesions. (These include, papillomas, granulomas, cysts, carcinomas, leukoplakia, Reinke's edema, polyps, vocal nodules, and subglottic stenosis.) The subject must be able to tolerate the entire pH study, and have accurately completed the diary that accompanies the pH study. In addition, they must be able to produce and collect the required throat/sputum samples for pepsin assay.

Exclusion Criteria:

Group 2.2 subjects must have one of the inflammatory or neoplastic lesions of the larynx, listed above; subjects with any other lesions will be excluded. Specifically excluded will be any patient/subject with airway obstruction, unless a tracheotomy tube is in place. In addition, respondents who indicate that they cannot produce any throat mucus (LSQ #24) are excluded.

The protocol for this Groups 2.1 and 2.2 will be similar to that of the other groups.

EXAMPLE 7

Clinical Trials in Patients with Respiratory Diseases

The specific aims of the exemplary clinical studies outlined in this and the following example are as follows:
(1) By accessing separate symptomatic cohorts, examine ranges of pepsin and pH levels among participants with pulmonary and respiratory disease (asthma and carcinoma of the lung);
(2) Examine the impact of disease type and severity on pepsin and pH levels.

These subjects are recruited for inclusion in this study from the Department of Pulmonary Medicine, Bowman Gray School of Medicine. Patient roles are generated and prospective participants who meet the eligibility criteria are randomly sampled and processed similar to those described in Example 6. Two discrete cohorts will be studied: Group 3.1- - - Asthma group and Group 3.2 - - - Carcinoma of the lung group.

Group 3.1 - - - Asthma Group (N=30) Inclusion Criteria:

To be included, the subject must have well-documented asthma, and they must be able to tolerate the entire pH study, and have accurately completed the diary that accompanies the pH study. In addition, they must be able to produce and collect the required throat/sputum samples for pepsin assay.
Exclusion Criteria:

Group 3.1 subjects must not any have other primary lung disease, and they must not have had asthma-related airway obstruction requiring hospitalization for the six-month period preceding inclusion in this study. In addition, respondents who indicate that they cannot produce any throat mucus (LSQ #24) will be excluded.

Group 3.2- - - Carcinoma of the Lung Group (N=30) Inclusion Criteria:

To be included, the subject must have biopsy-proven squamous cell carcinoma of the larynx, and they must be able to tolerate the entire pH study, and have accurately completed the diary that accompanies the pH study. In addition, they must be able to produce and collect the required throat/sputum samples for pepsin assay.
Exclusion Criteria:

Group 3.2 subjects must not any airway obstruction, hemoptysis, or metastatic disease in the head and neck. In addition, inclusion in this study cannot interfere with, or delay, treatment for the lung cancer. In addition, respondents who indicate that they cannot produce any throat mucus (LSQ #24) will be excluded.

The protocol for this Groups 3.1 and 3.2 will be similar to that of the other groups, Examples 5 and 6, and these subjects will be compensated for their participation in the study.

Sample Size Justification

It is important to demonstrate that the planned sample sizes will be sufficient to provide estimates that are fairly precise and to yield sufficient "power" for the planned inferences. As describe above, Example 5, up to 300 asymptomatic normal individuals may be used in a clinical trial. To gauge the adequacy of this sample size to characterize the distribution of pepsin levels in the population at large, a small simulation study was conducted. One hundred samples of size 300 were drawn from a normal distribution.

Table 5 lists the distribution of the true percentiles of the observed empirical percentiles from these samples:

TABLE 5

Results of simulation to determine expected distribution where N = 300

| Empirical Percentile | Distribution of True Percentiles: Empirical 95% Confidence Interval |
|---|---|
| 10 | 7.3–12.1 |
| 25 | 21.4–28.4 |
| 50 | 45.6–54.3 |
| 75 | 70.7–79.1 |
| 90 | 87.8–92.5 |

The simulation study indicates that 300 subjects should be sufficient to ensure that observed percentiles from the clinical trials are +5 percentiles from their target estimate. A sample of this size is sufficient to detect mean differences of 0.32 standard deviation units (SD) between genders (50% split), 0.34 SD between smokers (35/65% split), and between 0.36 SD African-Americans and Caucasians (30% and 65% of the cohort, respectively), and to detect correlations of $\pm 0.16$, with 80% statistical power.

Recruitment of 100 participants with laryngeal disease and 60 with pulmonary/respiratory disease allows for the ability to detect mean differences from the asymptomatic controls of one-third and one-half standard deviation units with greater than 80% statistical power.

Statistical Analyses

The panel of pepsin levels for each participant is described with plots and means. For meeting the major goals of the study, a summary statistic to describe overall pepsin levels is generated. This statistic is expected to be the average across all measures, however one might expect that the maximum and range might also have some clinical relevance. Principal components analyses and plots are used to explore patterns in these data and may define several summary measures to provide general expressions of pepsin levels. In the following descriptions of analyses, these outcome measures are succinctly referred to as "pepsin levels".

Normal ranges for pepsin levels

Means, standard deviations, percentiles and histograms are used to describe the distribution of pepsin levels from the asymptomatic participants, and in subgroups defined by gender and ethnicity. Asymmetric least squares (Efron, 1991) will be used to develop percentile plots across the age range.

Impact of LPR disposition, and other factors on pepsin and pH measures

Analyses of variance and regression methods are used to explore the impact of LPR questionnaire scores and individual demographic, history and lifestyle measures on pepsin and pH levels. Multivariable regression models are developed using (stepdown and step-up) selection processes. Depending on their empirical distributions, measures may be transformed to yield symmetric residuals distributions, however resultant estimates and standard errors are transformed back to their original scale using the delta method (Aickin, 1983).

Agreement between pepsin and pH measures among asymptomatic participants

Agreement is described using scatterplots and correlation coefficients. The impact of various predictors on the relationships between pepsin and pH are assessed using regression models involving two-way interactions and graphically. Canonical correlation are also used to explore the multivariable relationship that these measures have with predictors.

Impact of laryngeal and pulmonary/respiratory disease on pepsin and pH measures and ability of measures to characterize disease Analyses of variance and regression are used to explore the impact that disease, disease type, and disease severity have on pepsin and pH levels. Discriminant analyses are used to develop empirical diagnostic criteria based on each measure separately and in a multivariable fashion combining information across measures and questionnaire responses. Analyses are repeated separately for major subgroups of participants (e.g. based on gender and race). To explore the robustness of these diagnostic rules, the analysis is repeated using classification and regression tree (CART) analyses (Breiman et al., 1984) which requires fewer parametric assumptions.

Additional analyses may used to assess the internal and external validity of the LSQ questionnaire, to examine relationships between individual symptoms and predictors, and the repeatability and reliability of the pepsin and pH measures. Since no "gold standard" exists for defining LPR based on clinical measures and participant responses, latent variable analyses (e.g. factor analysis) may be used to attempt to characterize this underlying phenomenon from the predictive measures and symptoms.

Data Management

Interviewer-reviewed questionnaire data are collected in a systematic fashion by the study coordinator according to a written study protocol that enhances completeness and consistency. Each participant is assigned a unique study identification code (ID); participant identifiers (name, address, and contact information) is collected on a separate form and is not entered onto the computerized database to enhance confidentiality. Specimens are labeled with the ID and are analyzed by personnel masked to other study data.

Computerized data management occurs at the Section on Biostatistics, which has extensive experience in managing data from biomedical studies. Questionnaire data is double-keyed using software (FoxPro™) programs that include automatic range and logic checks; any discrepancies between keyed copies are resolved by hand. Laboratory data are computerized directly. Data are merged into a single study database which is maintained by the study programmer. Regular edits and reports are generated to assess consistency and study progress. Forms are stored securely in locked cabinets; all computerized databases are password-protected and stored in a secure manner consistent with procedures developed in the Section on Biostatistics for other studies.

EXAMPLE 8

Longitudinal (Daily) Investigations of Pepsin Levels in Airway Secretions

In order to determine if cyclic or lifestyle dependent changes occur, a subset of volunteers (with and without LPR) are asked to supply throat/sputum samples on a daily basis for one month. Two samples are obtained each day, one at rising in the morning, and the other before bedtime.

Criteria for inclusion/exclusion, procedures and statistical analyses are as in the previous examples.

EXAMPLE 9

Measurement of Serum and Urine Pepsin Levels in Patients with Ulcerative Esophagitis Patients with significant inflammatory disease may have abnormally high concentrations of pepsin/pepsinogen in their bloodstream. Measuring the levels of pepsins and pepsinogens in both urine and blood serum will determine is this is true. If this is the case then serum or urinary pepsin levels might be used as measures of the effectiveness of treatment in all reflux-related disease including esophagitis.

Preliminary data on the serum and urine pepsin levels of patients with (biopsy-proven) ulcerative esophagitis, before, during, and after treatment may be collected using the present invention and conventional methodology. Twenty patients will be monitored as well as 20 normal controls. The purpose of this study is to determine if (1) esophageal inflammation results in systemic absorption of measurable abnormally high amounts of pepsin and (2) whether or not these levels return to "normal" after treatment.

EXAMPLE 10

Longitudinal Investigation of LPR in Pediatric Subjects

Based upon preliminary work, using double-probe pH-testing, it has been determined that reflux may play an important role in the development and course of airway and respiratory diseases in children. Unfortunately, due to the invasiveness and expense of pH-testing, it is not possible to obtain normal values in a large population of healthy infants and children.

In this example, airway secretions of 1500 newborn infants (at birth and prior to discharge from the hospital) are screened with the present invention, and these patients are followed longitudinally at two-month intervals (at the times of regularly scheduled visits to the pediatrician) using sequential, "random" pepsin assays for at least 6 months.

At the six-month visit, a standard "symptom/illness" questionnaire (to collect data about any possible "reflux-related" airway and respiratory diseases) is completed by the infant's parents with the help of the pediatrician. The pepsin assay data and the clinical data are then analyzed to determine if the pepsin level predicts the development of airway disease.

Monitoring is done over the course of a year, and if results suggest that there is a relationship between the pepsin level and the development of airway disease, the initial group of subjects will be followed beyond six months, and the monitoring will expand to include a larger number of newborn infants; and screening of school-age children will begin.

EXAMPLE 11

Immunodetection Kits

In certain broad aspects, the present invention concerns immunodetection kits for use in the methods described herein. As the anti-pepsin antibodies are employed to detect pepsins and/or pepsinogens, either or both of such components may be provided in the kit. The immunodetection kits thus comprise, in suitable container means, an anti-pepsin or pepsinogen antibody and an immunodetection reagent.

Further suitable immunodetection reagents for use in the present kits may include a two-component reagent that comprises a secondary antibody that has binding affinity for the first antibody, and possibly a third antibody that has binding affinity for the second antibody. The last antibody used, either the first, second or third as the case may be, being linked to a detectable label.

A number of exemplary labels are known in the art and all such labels may be employed in connection with the present invention. To provide a detecting means, one of the antibodies has an associated label to allow detection. Preferably, this is an enzyme that generates color development upon incubating with an appropriate chromogenic substrate, such as a urease, glucose oxidase, alkaline phosphatase or hydrogen peroxidase.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

The kits may further comprise a suitably aliquoted composition of the pepsin or pepsinogen protein, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

The kits may further comprise a means for obtaining a sample from a subject. Such a means may include a swab, or a test-strip as described herein.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aickin M. Linear Statistical Analysis of Discrete Data. New York: Wiley, 1983

Axelsson, C. K., M. D. Nielsen, and A. M. Kappelgaard. Solid-phase double-antibody radioimmunoassay of pepsinogen I in serum. Clin Chim Acta 121:309–319, 1982.

Baccino, E., Le Goff, D., Lancien, G., et al.: Exploration of Acid Gastroesophageal Reflux by 24-h pH Metry in Infants at Risk of Sudden Infant Death Syndrome: A Study of 50 Cases. Forensic Sci Int 36:255–260, 1988.

Breiman L, Friedman JH, Olshen RA, Stone CJ. Classification and Regression Trees. Monterey, Calif: Wadsworth, 1984

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Castell D. O., Richter J. E. Editorial: Esophageal Symptoms and the "Irritable Esophagus." Dysphagia2:109–111, 1987

Cherry J., Margulies S. I. Contact ulcer of the larynx. Laryngoscope 78:1937–1940, 1968

Delahunty J. E. and Cherry J. Experimentally produced vocal cord granulomas. Laryngoscope78:1941–1947, 1968

Doellgast, G. J. Enzyme-linked coagulation assay. IV. Sensitive sandwich enzyme-linked immunosorbent assays using russell's viper venom factor X acitvator-anitbody conjugates. Analyt Biochem 167:97–105, 1987

Doellgast, G. J. Triscott M. X., Beard G. A., Bottoms J. D., Roh B. H., Roman M. G., Hall P. A., Brown J. E. Sensitive ELISA for detection of C. botulinum neurotoxins A, B and E using signal amplification via enzyme-linked coagulation assay. J Clinical Microbiol 31:2402–2409, 1993.

Doellgast, G. J., Beard G. A., bottoms J. D., Cheng T., Roh B. H., Roman M. G., Hall P. A., Triscott M. X. Enzyme-linked immunoabsorbent assay and enzyme-linked coagulation assay for detection of C. botulinum neurotoxins A, B and E and solution-phase complexes with "dual-label" antibodies. J Clinical Microbiology 32:105–111, 1994

Durkee KH, Roh BH, Doellgast GJ. Immunoaffinity chromatographic purification of a russell's viper venom factor X activator using elution in high concentrations of magnesium chloride. Protein Expression and Purification 4:405–411, 1993

Efron B. Regression percentiles using asymmetric squared error loss. Statistica Sin 1:93–126, 1991

Flores TC, Cross FS, Jones RD. Abnormal Esophageal Manometry in Globus Hystericus. Ann Otol Rhinol Laryngol 90:383–386, 1981

Gefter et al, Somatic Cell Genet. 3:231–236 (1977)

Gerhardt DC, Shuck TJ, Bordeaux EA, et al. Human upper esophageal sphincter. Response to volume, osmotic, and acid stimuli. Gastroenterol 75:268–274, 1978

Goding, 1986, in Monoclonal Antibodies: Principles and Practice, 2d ed., Orlando, Fla., Academic Press, 1986, pp. 60–61, 65–66, 71–74.

Herbst, J. J., Minton, S. D. and Book, L. S.: Gastroesophageal Reflux Causing Respiratory Distress and Apnea in Newborn Infants. J Pediatr, 95:763–768, 1979.

Hirschowitz BI. A critical analysis, with appropriate controls, of gastric acid and pepsin secretion in clinical esophagitis. Gastroenterol 101:1149–1158, 1991

Huang, S. C., K. Miki, K Hirano et al Enzyme-linked immunosorbent assay of serum pepsinogen I. Clin Chim Acta 162:85–96, 1987.

Huang, S. C., K. Miki, C. Furihata, M. Ichinose, A. Shimizu and H. Oka. Enzyme-linked immunosorbent assays for serum pepsinogens I and II using monoclonal antibodies - - - with data on peptic ulcer and gastric cancer. Clin Chim Acta 175:37–50, 1988.

Johnson L. F., Harmon J. W. Experimental Esophagitis in a Rabbit Model. Clinical Relevance. J Clin Gastroenterol 8(Suppl 1):26–44, 1986

Kahrilas PJ, Dodds WJ, Dent J, et al. Effect of sleep, spontaneous gastroesophageal reflux and a meal on upper esophageal sphincter pressure in normal human volunteers. Gastroenterol 92:466–471, 1987

Kohler and Milstein, Nature 256:495–497 (1975)

Kohler and Milstein, Eur. J. Immunol. 6:511–519 (1976)

Koufman JA, Wiener GJ, Wu WC, Castell DO. Reflux laryngitis and its sequelae: the diagnostic role of ambulatory 24-hour pH monitoring. J Voice 2:78–89, 1988

Koufman JA. The otolaryngologic manifestations of gastroesophageal reflux disease. Laryngoscope 101: (Supplement 53) 1–78, 1991

Koufman JA. Editorial: Aerodigestive Manifestations of Gastroesophageal Reflux: What We Don't Yet Know. Chest 104:1321–1322, 1993

Koufman JA. The otolaryngologic manifestations of gastroesophageal (laryngopharyngeal) reflux disease. The Instructional Courses of The American Academy of Otolaryngology - - - Head and Neck Surgery, Volume 8, Edited by Lucente et al., Mosby, Philadelphia, pages 57–67, 1996

Lillemoe K. D., Johnson L. F., Harmon J. W. Role of the Components of the Gastroduodenal Contents in Experimental Acid Esophagitis. Surgery 92:276–284, 1982

Little FB, Koufman JA, Kohut RI, Marshall RB. Effect of gastric acid on the pathogenesis of subglottic stenosis. Ann Otol Rhinol Laryngol 94:526–519, 1985

Miki K, Ichinose M, Shimizu A, et al. Serum pepsinogens as a screening test of extensive chronic gastritis. Gastroenterologia Japonica 22:133–141, 1987

Morrison MD. Is chronic gastroesophageal reflux a causative factor in glottic carcinoma? Otolaryngol Head Neck Surg 99:370–373, 1988

Nakamura et al., Enzyme Immunoassays: Heterogeneous and Homogeneous Systems, Chapter 27, 1987

Neoh SH, Jahoda DM, Rowe DS, Voller A. Immunoglobulin classes in mammalian species identified by cross-reactivity with antisera to human inimunoglobulin. Immunochemistry 10:805–813, 1973

Ohman L, Olofsson J, Tibbling L, et al. Esophageal Dysfunction in Patients with Contact Ulcer of the Larynx. Ann Otol Rhinol Laryngol 92:228–230, 1983

Olson NR. The Problem of Gastroesophageal Reflux. Otolaryngol Clin North Am 19:119–133, 1986

Ossakow SJ, Etla G, Colturi T, et al.: Esophageal reflux and dysmotility as the basis for persistent cervical symptoms. Ann Otol Rhinol Laryngol 96:387–392, 1987

Paton, J. Y., MacFadyen, U. M. and Simpson, H.: Sleep Phase and Gastro-oesophageal Reflux in Infants at Possible Risk of SIDS. Arch Dis Child, 64:264–269, 1989.

Piper DW, Fenton BH. pH stability and activity curves of pepsin with special reference to their clinical importance. Gut 6:506–508, 1965

Richter JE, ed. Ambulatory Esophageal pH Monitoring: Practical Approach and Clinical Applications. Igaku-Shoin, Tokyo, 1991

Richter JE, Bradley LA, DeMeester TR, Wu WC, et al.: Normal 24-Hour pH values: Influence of study center, pH electrode, age, and gender. Dig Dis Sci 37:849-856, 1992

Samloff IM, Taggart RT. Pepsinogens, Pepsins, and Peptic Ulcer. Clin Invest Med 10:215–221, 1987

Stemmermann GN, Samloff IM, Heilbrun LK, Nomura A. Serum pepsinogens I and II and stomach cancer. Clin Chim Acta 163:191–198, 1987

Waldum HL, Straume BK, Burhol PG. Radioimmunoassay of group I pepsinogens (PG I) and the effect of food on serum PG I. Scand J Gastroenterol 14:241–247, 1979

Ward PH, Hanson DG. Reflux as etiological factor of carcinoma of the laryngopharynx. Laryngoscope 98:1195–1199, 1988

Wiener GJ, Cooper JB, Wu WC, et al. Is hoarseness an atypical manifestation of gastroesophageal reflux (GER)? An ambulatory 24 hour pH study. (Abstract) Gastroenterol 90A:1691, 1986

Wiener GJ, Koufman JA, Wu WC, Copper JB, Richter JE, Castell DO. The pharyngo-esophageal dual ambulatory pH probe for evaluation of atypical manifestations of gastroesophageal reflux (GER). Gastroenterol 92:A1 694, 1987

Wiener GJ, Koufman JA, Wu WC, et al. Chronic hoarseness secondary to gastroesophageal reflux disease: documentation with 24-hour ambulatory pH monitoring. Am J Gastroenterol 84:1503–1508, 1989

What is claimed is:

1. A method of diagnosing a gastric reflux event comprising detecting pepsin or pepsinogen in an extraesophageal or laryngeal area of a subject.

2. A method according to claim 1, wherein said gastric reflux is indicative of a extraesophageal reflux disease.

3. A method according to claim 2, wherein said gastric reflux is indicative of a laryngopharyngeal reflux disease.

4. A method according to claim 1, wherein said detecting is by immunoassay.

5. A method according to claim 4, wherein said immunoassay comprises contacting a sample with an antibody immobilized on a solid support.

6. A method according to claim 5, wherein said antibody is a chicken antibody preparation immunoreactive with human pepsin, pepsinogen or both.

7. A method according to claim 5, wherein said antibody is a human antibody preparation immunoreactive with human pepsin, pepsinogen or both.

8. A method according to claim 4, wherein said immunoassay is a radioimmunoassay.

9. A method according to claim 5, wherein said solid support is inserted into the throat of said subject.

10. A method according to claim 9, wherein said solid support is affixed to an endoscope, aspirator, pH catheter, a nasogastric tube or an endotracheal tube.

11. A method of diagnosing a gastric reflux disorder comprising:

obtaining a sample from a subject suspected of having a gastric reflux disorder;

contacting said sample with an antibody immunoreactive with human pepsin and/or pepsinogen;

detecting said immunoreaction; and comparing said immunoreaction to a standard immunoreaction level;

wherein an increase in immunoreaction in said sample compared to said standard is indicative of a gastric reflux disorder.

12. A method according to claim 11, wherein said sample is an expectorate.

13. A method according to claim 11, wherein said sample is a saliva sample.

14. A method according to claim 11, wherein said sample is from an airway mucosa of said subject.

15. A method according to claim 11, wherein said sample is taken from the area between the lower esophageal sphincter and the upper esophageal sphincter of said subject.

16. A method according to claim 11, wherein said sample is taken from the area above the upper esophageal sphincter of said subject.

17. A method according to claim 11, wherein a sample is taken from the area between the lower esophageal sphincter and the upper esophageal sphincter of said subject and a sample is taken from the area above the upper esophageal sphincter of said subject.

18. A method according to claim 11, wherein said sample is a serum or urine sample.

19. A method according to claim 11, wherein said detecting is by a calorimetric label attached to said antibody.

20. A method according to claim 11, wherein said detecting is by a fluorescent label attached to said antibody.

21. A method of diagnosing a gastric reflux disorder comprising:

obtaining a sample from an extraesophageal area of a subject suspected of having a gastric reflux disorder;

detecting the level of pepsin or pepsinogen in said sample; and comparing said level to a normal pepsin level;

wherein the presence of an above normal pepsin or pepsinogen level is indicative of a gastric reflux disorder.

22. A method according to claim 21, further defined as contacting said sample with an antibody immunoreactive with human pepsin or pepsinogen;

detecting said immunoreaction; and comparing said immunoreaction to a standard immunoreaction level;

wherein an increase in immunoreaction in said sample compared to said standard is indicative of a gastric reflux disorder.

23. A method according to claim 21, wherein said extraesophageal area is lung, blood vessel, mouth, airway, throat or urinary tract.

* * * * *